United States Patent
Thoms

(10) Patent No.: US 8,102,965 B2
(45) Date of Patent: Jan. 24, 2012

(54) PANORAMIC RECORDING DEVICE FOR A PANORAMIC X-RAY MACHINE

(75) Inventor: Michael Thoms, Bietigheim-Bissingen (DE)

(73) Assignee: Michael Thoms (DE)

( * ) Notice: Subject to any disclaimer, the term of this patent is extended or adjusted under 35 U.S.C. 154(b) by 0 days.

(21) Appl. No.: 11/910,514

(22) PCT Filed: Mar. 22, 2006

(86) PCT No.: PCT/EP2006/002619
§ 371 (c)(1),
(2), (4) Date: Apr. 8, 2008

(87) PCT Pub. No.: WO2006/105868
PCT Pub. Date: Oct. 12, 2006

(65) Prior Publication Data
US 2008/0187096 A1    Aug. 7, 2008

(30) Foreign Application Priority Data
Apr. 5, 2005 (DE) .......................... 10 2005 015 707

(51) Int. Cl.
*A61B 6/14* (2006.01)
(52) U.S. Cl. ............................ 378/38; 378/39; 378/40
(58) Field of Classification Search ............... 378/38–40
See application file for complete search history.

(56) References Cited

U.S. PATENT DOCUMENTS

| | | | |
|---|---|---|---|
| 4,878,234 A * | 10/1989 | Pfeiffer et al. | ................... 378/40 |
| 5,793,838 A | 8/1998 | Kovacs | |
| 5,844,961 A | 12/1998 | McEvoy et al. | |
| 6,173,035 B1 * | 1/2001 | Tachibana et al. | .............. 378/39 |
| 2002/0041652 A1 | 4/2002 | Suuronen | |
| 2003/0202636 A1 * | 10/2003 | Thoms | ......................... 378/184 |

FOREIGN PATENT DOCUMENTS

| | | |
|---|---|---|
| DE | 9421296 U1 | 2/1996 |
| DE | 10148412 A1 | 5/2002 |
| EP | 0904734 A2 | 3/1999 |
| GB | 2 274 964 A | 8/1994 |
| WO | 9805256 A1 | 2/1998 |

* cited by examiner

*Primary Examiner* — Hoon Song
*Assistant Examiner* — Mona M Sanei
(74) *Attorney, Agent, or Firm* — Factor Intellectual Property Law Group, Ltd.

(57) ABSTRACT

In order to set up digital image acquisition in classic panoramic X-ray machines, the invention proposes providing a row of detectors in the cartridge unit of the machines, said row of detectors being arranged or being able to be arranged behind the recording slit. The output signals from the row of detectors and the output signals from a rotary encoder are wirelessly transferred to an evaluation unit. Retrofitting the digital image acquisition thus does not require any intervention in safety-related parts of the panoramic X-ray machine.

14 Claims, 5 Drawing Sheets

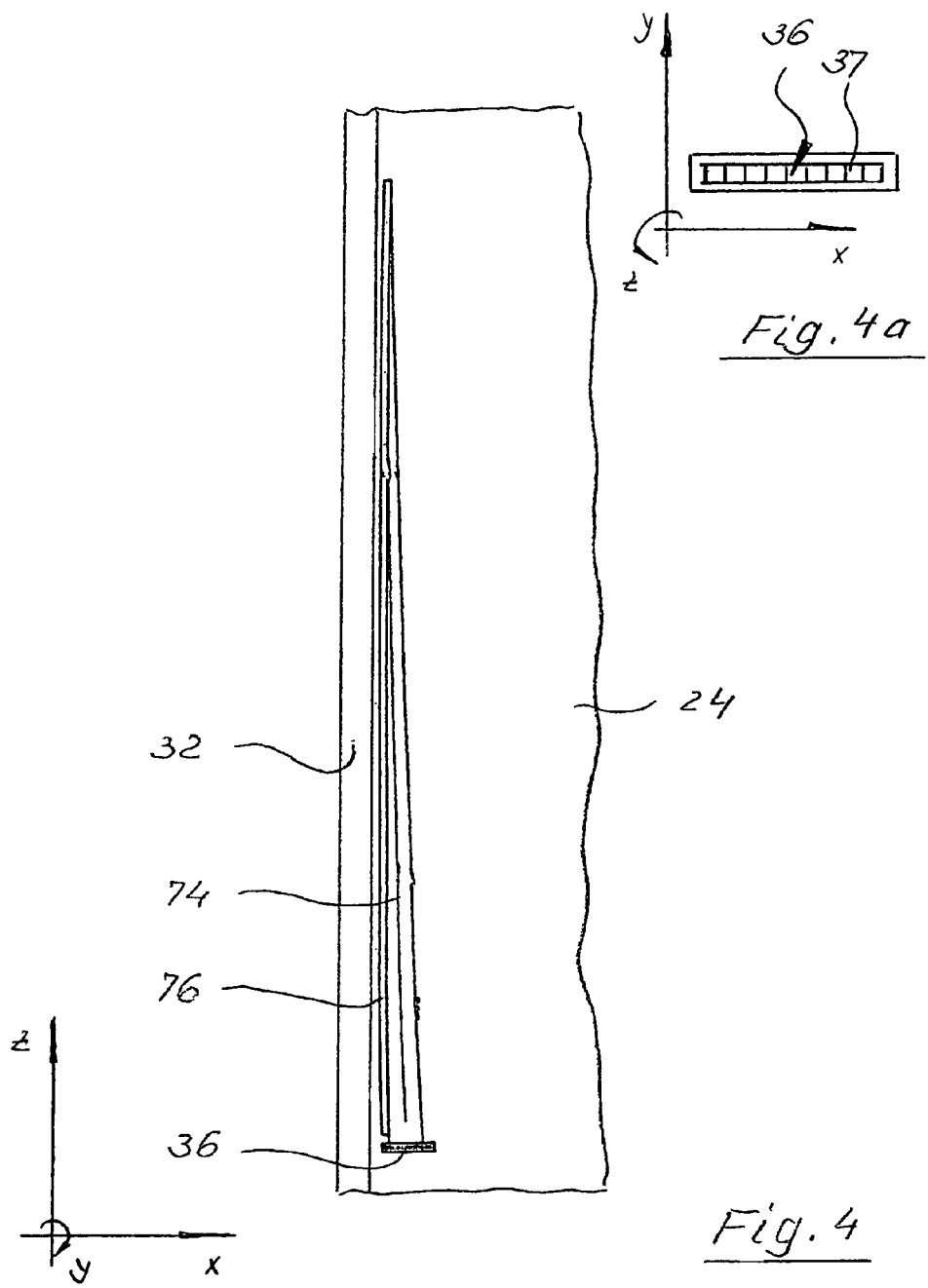

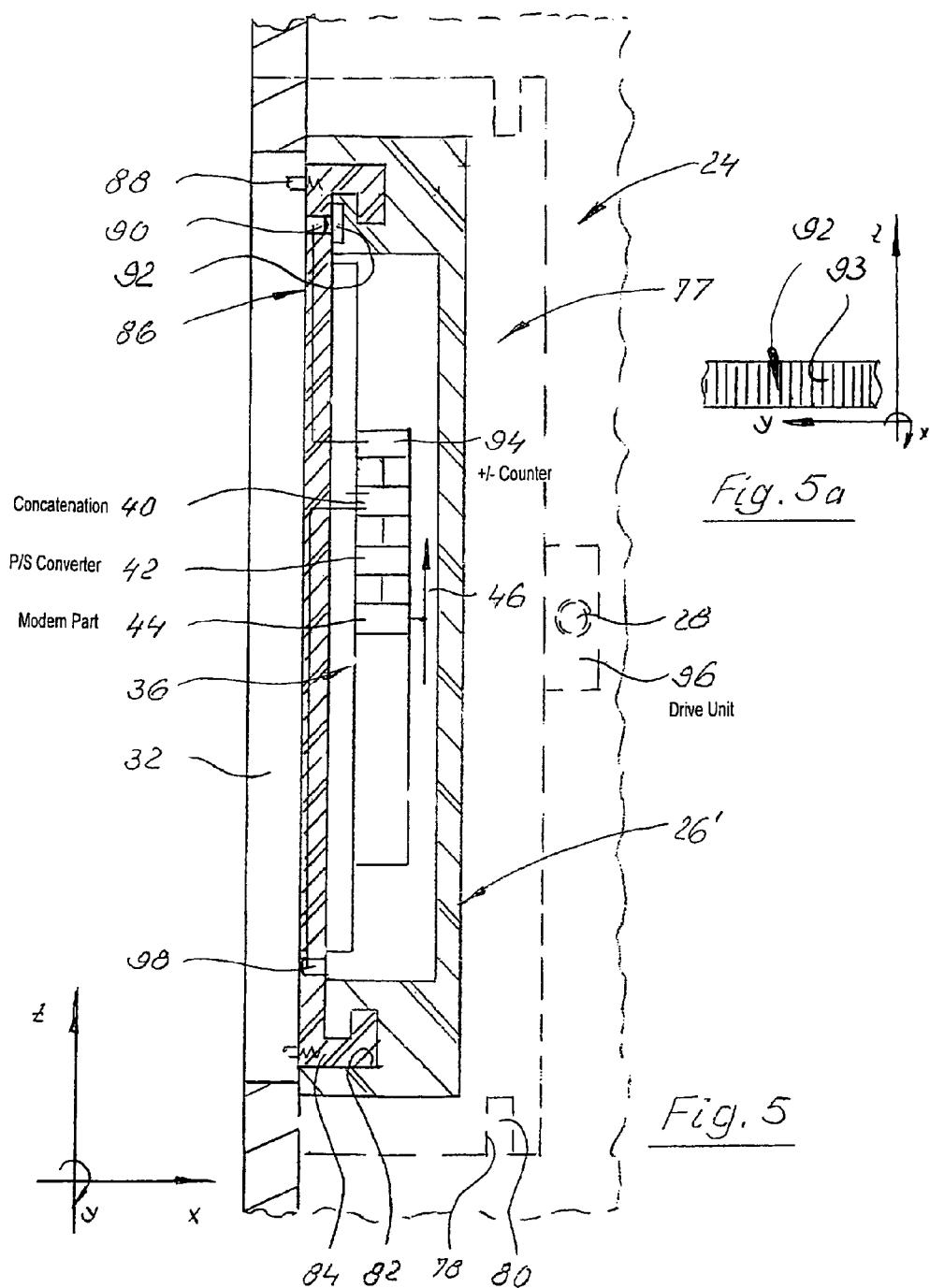

PANORAMIC RECORDING DEVICE FOR A PANORAMIC X-RAY MACHINE

RELATED APPLICATIONS

This application claims the filing benefit of PCT Patent Application PCT/EP2006/002619, filed Mar. 22, 2006, which claims the filing benefit of German Patent Application Number 10 2005 015 707.6, filed on Apr. 5, 2006; the contents of all of which are incorporated herein by reference.

TECHNICAL FIELD

The present invention concerns a panoramic recording device for a panoramic X-ray machine, with a cartridge unit which has a recording slit, and with an X-ray detection device which is arranged behind the recording slit, and with means to capture the position of the cartridge unit, wherein the detection device includes at least one detector row which is shaped according to the shape of the recording slit, and which is provided with a readout circuit, that the position acquisition means provides an electrical output signal which corresponds to the rotary position, and that the output signals of the detector row and position acquisition means are transmitted wirelessly to a processing unit.

BACKGROUND OF THE INVENTION

Classic panoramic X-ray machines have an X-ray source and a panorama cartridge, which can be pivoted together around an axis, which is usually vertical. Between the X-ray source and the panorama cartridge, an object to be investigated, e.g. a patient's jaw, is positioned.

A film holder, which is arranged in the cartridge, is movably arranged in the cartridge behind a recording slit, and is moved past the recording slit depending on the angle of rotation of the arm which joins the X-ray gun and panorama cartridge.

In this way, a panoramic image of the object, resulting from individual slit images being joined one behind another, is obtained on the film.

For various reasons, recording X-ray images with sensors which provide electrical signals is increasingly preferred to generating them with classic silver films. In this way the films, which contain silver, are not needed, the images can be processed electronically, and archiving the recordings is also simplified.

Panoramic X-ray machines are relatively expensive devices with a high expected lifetime.

There is therefore interest in, on the one hand, being able to continue to use the expensive equipment which already exists, and on the other hand, being able to use the advantages of modern digital image processing.

Retrofit kits for panoramic machines with film cartridges, a CCD line array being fixed to the cartridge, have already been offered on the market. However, the cable looms of the sensor are connected to the panoramic X-ray machine. Legally, this must be classified as an intervention in the machine, so that according to the law on medical products, the machine must be completely re-accepted after the conversion. For this purpose, among other things, a safety test is required, and this makes it necessary to transport the machine back to the manufacturer. Further tests are also necessary there. The effort for such a retrofit is therefore high, and the retrofit is expensive. Another reason for this is that a CCD sensor which is arranged on the cartridge must be guided past multiple mechanical pivotal points, and these can only be produced in small numbers, since the relevant CCD sensors are always manufacturer-specific and many competitors with different machines divide the market.

Typically, panorama cartridges according to DIN 6832, Part 1 have a low thickness of about 15 mm with external dimensions of about 160×330 mm (nominal size of cartridge 13×30 cm) or 180×330 (nominal size 15×30 cm).

The present invention is directed to resolving these and other matters.

SUMMARY OF THE INVENTION

The present invention is intended to be an enhanced panoramic recording device wherein the detection device includes at least one detector row which is shaped according to the shape of the recording slit, and which is provided with a readout circuit, that the position acquisition means provides an electrical output signal which corresponds to the rotary position, and that the output signals of the detector row and position acquisition means are transmitted wirelessly to a processing unit, so that with it the advantages of digital image processing are obtained, but a repeated acceptance of the whole panoramic X-ray machine is unnecessary.

According to the invention, this object can be achieved by a panoramic recording device for a panoramic X-ray machine, with a cartridge unit which has a recording slit, and with an X-ray detection device which is arranged behind the recording slit, and with means to capture the position of the cartridge unit, characterized in that the detection device includes at least one detector row which is shaped according to the shape of the recording slit, and which is provided with a readout circuit, that the position acquisition means provides an electrical output signal which corresponds to the rotary position, and that the output signals of the detector row and position acquisition means are transmitted wirelessly to a processing unit.

In the case of the panoramic recording device according to the invention, a row of detectors which has pixels which are arranged one behind another according to the longitudinal extent of the recording slit is built into the panorama cartridge as a light detector. The output signals of the row of detectors are read out wirelessly (by radio or infrared radiation) and transmitted to a processing unit. The position of the panorama cartridge in space (or with reference to the object at rest) is measured by a position sensor (position capturing means), and its output signal is passed, also wirelessly, to the evaluation unit. The processing unit can then combine the image lines in a memory, line by line, into the total image, using the output signal of the position sensor as an addressing signal.

Because the data transmission to the processing unit takes place wirelessly, and the row of detectors and position encoder and the electronic components which are connected to them are operated from a battery, a galvanic connection between the row of detectors and the panoramic X-ray machine is unnecessary.

This means that at the acceptance of a classic panoramic X-ray machine which is converted to digital image acquisition, only the image quality has to be demonstrated according to the X-ray regulation, but a risk assessment according to the medical product law can be omitted, because work with the cartridge was already included in the use of the classic panoramic X-ray machine as stipulated.

A panoramic recording device according to the invention can be implemented with little wiring effort and thus low cost.

The panorama cartridge which is provided with a row of detectors which are read out wirelessly can be offered in the standard sizes according to DIN. Such a cartridge is thus compatible with all corresponding classic panoramic X-ray machines. The panoramic recording device according to the invention can thus be sold in larger numbers, which reduces production costs and thus retrofit costs.

Advantageous further developments of the invention are given in the subclaims.

The further development of another embodiment of the present invention, e.g., in which the processing unit includes a memory, the memory cells of which store the image signals which the detector row provides, being addressed by a signal which is derived from the output signal of the position acquisition means, makes it possible, very simply, to combine the individual slit-shaped partial images into a total image as soon as the individual image lines are stored.

The further development of another embodiment of the present invention, e.g., in which the position acquisition means is provided on the cartridge unit, and the output signals of the detector row and position acquisition means are combined via a concatenation circuit into a data packet, which is transmitted via a single data transmission channel of the processing unit, makes it possible to achieve the transmission of both the image signals and the position signals with a single data transmission link. In this way too, the recording device becomes specially simple.

A further development of another embodiment of the present invention, e.g., in which the cartridge unit movably carries a first cradle, on which in its turn a second cradle which carries the detector row, and which is movable parallel to the first cradle, and which can be blocked by the recording slit is arranged, the processing unit includes a memory, the memory cells of which store the image signals which the detector row provides, being addressed by a signal which is derived from the output signal of the position acquisition means, makes it possible to put the detector row and the mechanism which carries it onto the X-ray machine, and to take it off again, as one unit, and yet to ensure a fixed position of the detector row with reference to the recording slit. The whole unit can have the same external geometry as a cartridge for a classic X-ray film.

According to another embodiment of the present invention, e.g., in which the position acquisition means includes a ruled grating which is supported by the cartridge unit, and a line reading head which is connected to the second cradle, the position of the detector row with reference to a cradle which carries it can be derived in a specially simple way from the mechanical driving movement for the classic cartridge.

Alternatively, in the panorama cartridge a signal corresponding to the angular position of the cartridge with reference to the axis of rotation of the machine can be obtained by using the mechanical output signal of a drive through which, in the case of the classic panorama cartridge, the film holder is pushed.

If, in the case of a panoramic recording device according to the present invention, the possibility of recording on a classic X-ray film is desired, the mechanical drive which acts on the film holder for digital image acquisition must be stopped, so that the detector row can remain permanently behind the recording slit. The mechanical connection between the axis of rotation of the machine and the film holder drive must therefore be interrupted. In such cases, it is then advantageous to provide the position sensor spatially separated from the panorama cartridge, and then to feed its output signal via a separate transmission channel to the processing unit, in that the position acquisition means is spatially separated from the cartridge unit, and the output signals of the detector row and position acquisition means are fed via separate transmission channels to the processing unit.

In the case of a cartridge unit according to another embodiment of the present invention, e.g., in which the cartridge unit has a film holder, which can be connected to or disconnected from the shaft which carries the cartridge unit, according to choice, by simply switching between the two working positions of a coupler, it is possible to switch between the classic method of operation with X-ray film and the method of operation with digital image acquisition.

In the case of a recording device according to another embodiment of the present invention, e.g., in which the detector row is connected to a fibre optic, the axis of which is inclined at a small angle to the axis of the recording slit, and which has an end surface which is essentially perpendicular to its axis, on which end surface the detector row is arranged essentially transversely to the longitudinal axis of the slit, a long recording slit is mapped onto a short detector row via the fibre optic, which is cut at a small angle. Short detector rows which are sensitive to visible light are obtainable on the market as relatively inexpensive components.

The further development of the invention according to another embodiment of the invention, e.g., in which the detector row is in the form of a narrow array, and that the detector readout circuit shifts the pixels of the column which runs parallel to the recording slit in the row direction according to the output signal of the position acquisition means, it is advantageous regarding the increase of the sensitivity of the recording unit. This makes it possible to work with smaller radiation doses.

It is to be understood that the aspects and objects of the present invention described above may be combinable and that other advantages and aspects of the present invention will become apparent upon reading the following description of the drawings and detailed description of the invention.

BRIEF DESCRIPTION OF THE DRAWINGS

FIG. 4 shows a cross-section through a detector row and the adjacent recording slit of a panoramic X-ray machine, the cross-section being through the centre of the slit; and, FIG. 4a is an enlarged view of the top side of the detector row of FIG. 4;

FIG. 5 shows a cross-section through a modified recording unit, in a plane which is perpendicular to the cartridge adjustment direction.

FIG. 5a is a top view of a section of a ruled grating forming part of the recording unit of FIG. 5.

DETAILED DESCRIPTION OF THE PRESENT INVENTION

Figure 1:
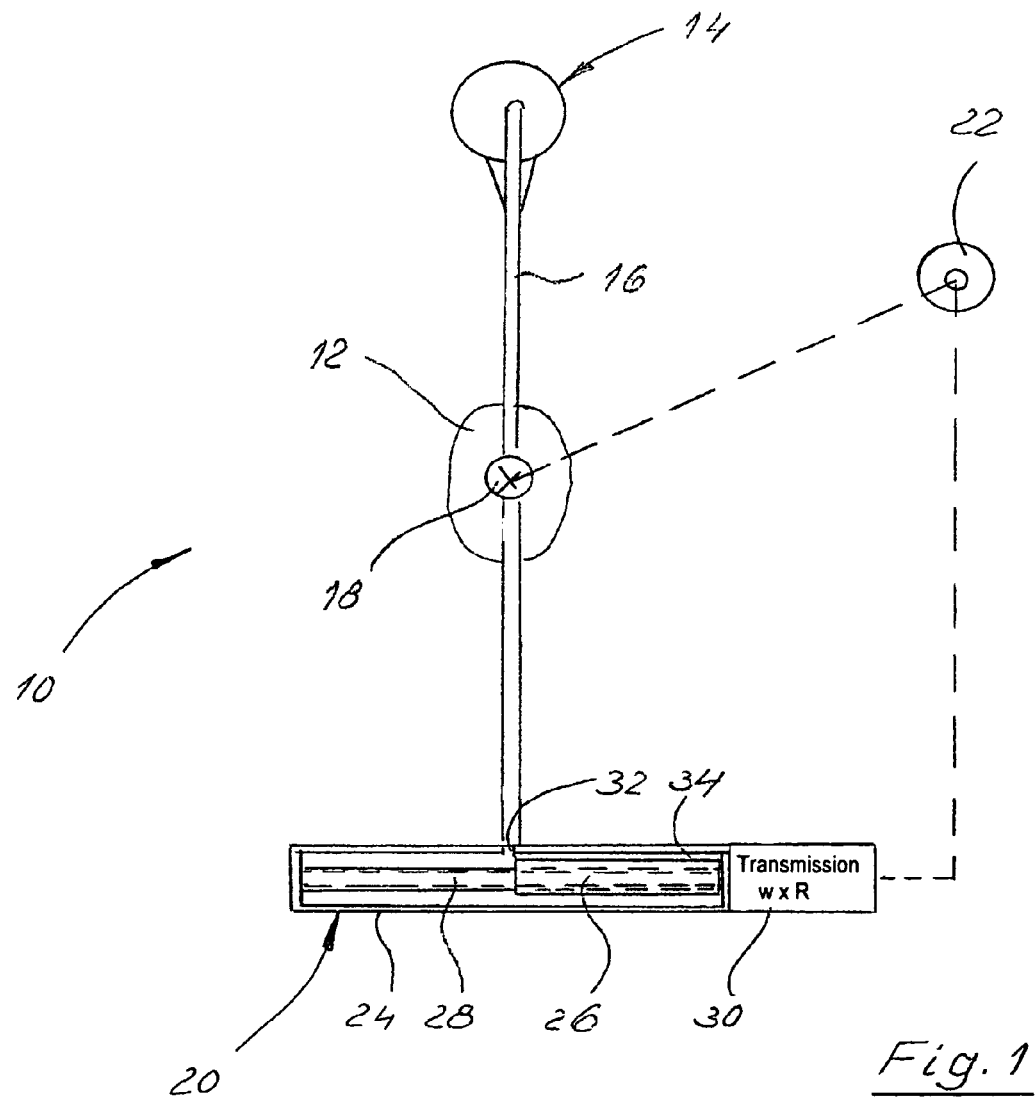
FIG. 1 shows a schematic representation of a panoramic X-ray machine which works with classic X-ray films.

While this invention is susceptible of embodiment in many different forms, there is shown in the drawings and will herein be described in detail one or more embodiments with the understanding that the present disclosure is to be considered as an exemplification of the principles of the invention and is not intended to limit the invention to the embodiments illustrated.

In FIG. 1, a panoramic X-ray machine is designated as a whole with 10, and an object to be investigated with 12.

The panoramic X-ray machine comprises an X-ray source 14, which has an X-ray tube, a housing which surrounds it and an outlet slit for X-ray light, as is known per se and not shown in more detail in the drawings. The X-ray source 14 is attached to a rod 16, which is supported by a shaft 18, which can be rotated around a usually vertical axis. The free end of the rod 16 supports a cartridge unit 20. The shaft 18 is made to rotate by a motor 22.

The cartridge unit 20 has a housing 24, in which a film holder 26 can be moved by means of a threaded spindle 28. The threaded spindle 28 is also coupled via a transmission 30 to the shaft of the motor 22.

In the wall of the housing 24 facing the X-ray source 14, a recording slit 32 is provided. Through it, X-ray light which has penetrated the object 12 can fall into the interior of the housing 24.

The transmission 30 is designed so that it pushes the film holder 26 by a distance equalling the angle of rotation w of the axis of the shaft 18 multiplied by the distance R between the recording slit 32 and the axis of the shaft 18.

If the rod 16 is rotated, those areas of the object 12 which are further from the axis of the shaft 18 are not sharply mapped. If what is wanted is to map an extended structure like a patient's jaw using the panoramic X-ray machine 10, the axis of the shaft 18 itself is moved by a mechanism (not shown in more detail) correspondingly to the curvature of the jaw.

In this way, when the rod 16 is rotated and the axis of the shaft 18 is moved, a flat X-ray image developed view of a jaw is obtained on a film 34, which is supported by the film carrier 26.

Figure 2:
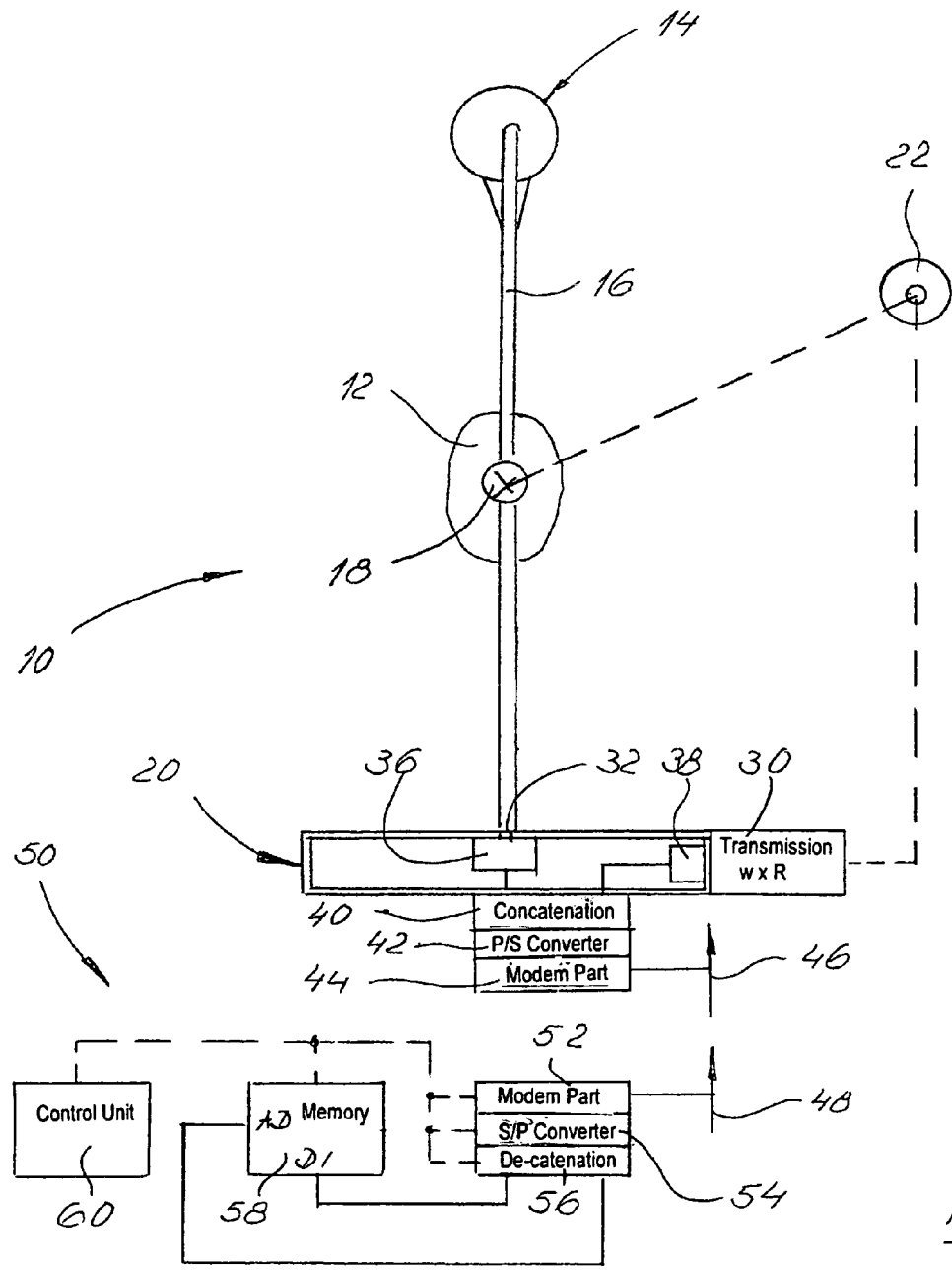
FIG. 2 shows a schematic representation of a panoramic X-ray machine which is similar to that of FIG. 1, but is retrofitted for digital image acquisition.

In the case of the panoramic X-ray machine shown in FIG. 2, components which are explained above with reference to FIG. 1 are again given the same reference symbols. These components do not need to be explained again in more detail.

Behind the recording slit 32, a detector row 36, the structure of which will be explained more precisely below with reference to FIG. 4, is arranged. The film holder 26 and its adjustment mechanism are removed, and the output of the transmission 30 is connected directly to a rotary encoder 38.

Let it be assumed here that the detector row 36 includes a readout circuit, and the rotary encoder 38 also contains a readout circuit. Let it also be assumed that the output signals of the detector row 36 and rotary encoder 38 are represented digitally in parallel.

A symbol concatenation circuit 40 is connected to the outputs of the detector row 36 and rotary encoder 38, and combines the two output signals into one data packet.

This is converted in a parallel/serial converter 42 into a sequence of bits, which are output via a modem part 44 to an aerial 46.

An aerial 48, which is part of a processing unit which is designated as a whole with 50, receives the signals of the aerial 46 and outputs them to a modem part 52. Via it, the signals reach a serial/parallel converter 54. At its output, the combined data packet is received back.

The output of the serial/parallel converter 54 is connected to the input of a symbol separating circuit 56, which separates the image signals which the detector row 36 generates from the output signal of the rotary encoder 38.

The thus regained output signal of the rotary encoder 38 is applied (after suitable scaling) to the address terminal AD of a memory 58, the data input terminal DI of which is connected to the other output of the symbol separating circuit 56, which provides the image signals.

A control unit 60 controls the sequence of the various substeps which are to be executed in the data transmission described above, and ensures correct synchronisation of the components.

Via the data transmission link, the control unit 60 can also output commands directly to the detector row 36 and rotary encoder 38, to cause them to output a new measured value.

It can be seen that with the panoramic recording device shown in FIG. 2, a digital X-ray image is obtained, without the necessity of intervening in the safety-relevant parts of the panoramic X-ray machine. In particular, the cartridge unit 20 has the same geometrical dimensions as the traditional film cartridge unit 20 according to FIG. 1, so that such a unit can easily be replaced by a cartridge unit with digital image acquisition.

Figure 3:
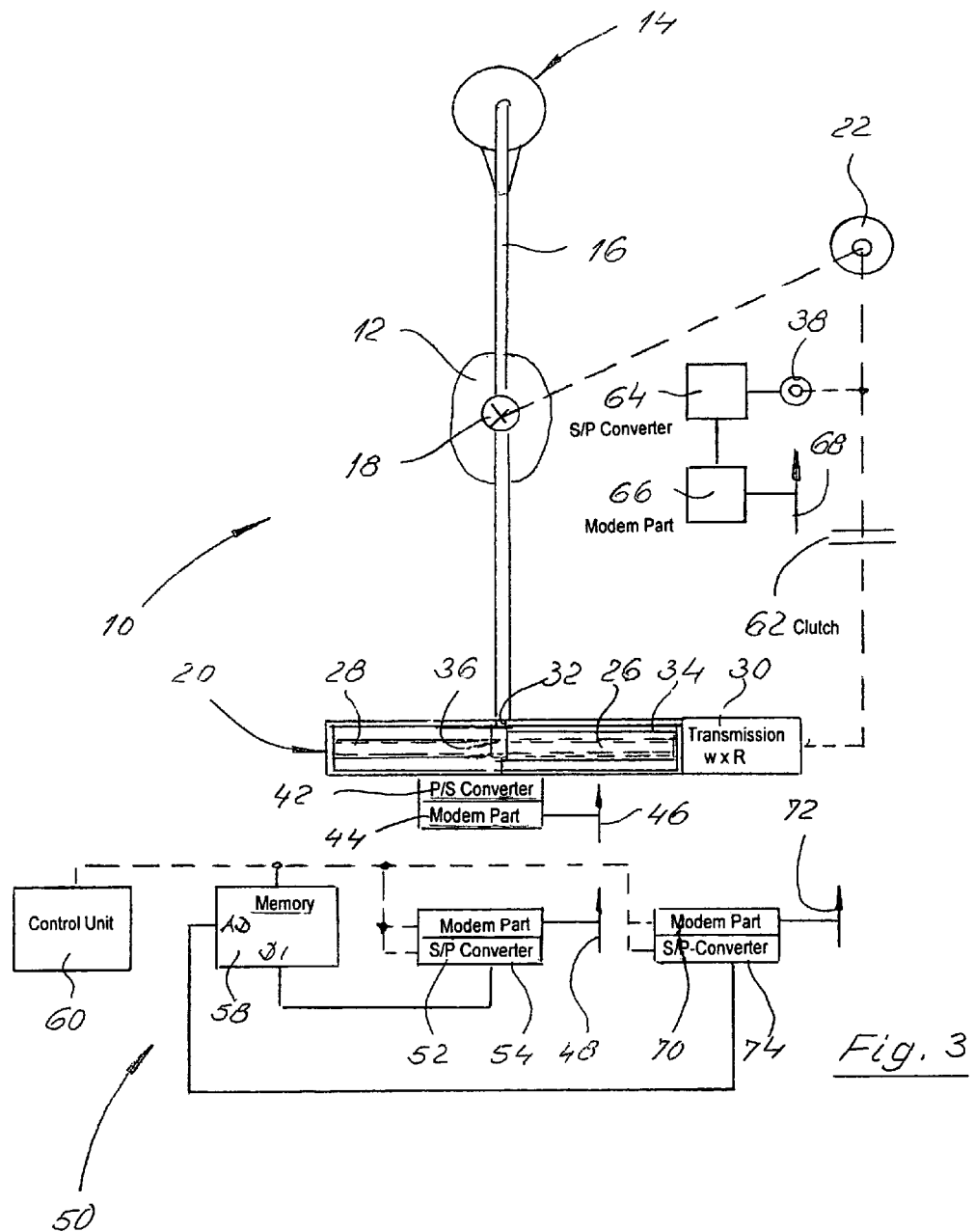
FIG. 3 shows a similar view to FIG. 1 of a panoramic X-ray machine, which however can work with both classic X-ray films and digital image acquisition.

In the case of the embodiment according to FIG. 3 too, device components which are explained above are again given the same reference symbols. These components do not need to be explained again in detail.

The panoramic X-ray machine according to FIG. 3 is very similar in its mechanical structure to that of FIG. 1, with the single exception that on the end of the film holder 26, a detector row 36, which is very short in the direction of movement of the film holder, is fitted.

Additionally, between the input of the transmission 30 and the shaft of the motor 22, a clutch 62 is provided.

If the clutch 62 has been opened and the detector row 36 has previously been moved into the position which is reproduced in the drawing, and in which it is behind the recording slit 32, it is possible to work with digital image acquisition. The necessary information about the angular position of the panoramic X-ray machine with reference to the object 12 is now obtained by the rotary encoder 38 being connected directly to the shaft of the motor 22.

Now, for the rotary encoder 38, its own serial/parallel converter 64 and its own modem part 66, to which an aerial 68 is connected, are provided. The modem part 66 works at a frequency which is different from that of the modem part 44, but which agrees with the frequency of another modem part 70, which receives via an aerial 72.

A serial/parallel converter 75 is connected to the modem part 70.

Thus in the data transmission link between the detector row 36 and the processing unit 50, the symbol concatenation circuit 40 and symbol separating circuit 56 can be omitted.

It can be seen that with the clutch 62 open, the panoramic X-ray machine shown in FIG. 3 supplies a digital panoramic image, like the panoramic X-ray machine according to FIG. 2, whereas with the clutch 62 closed, a film 34 can be exposed in the classic way, if the higher resolution of the X-ray film is required in special cases.

FIG. 4 shows how a slit-shaped X-ray image with a great vertical extent of the recording slit (about 15 cm) can be recorded using a detector row 36 with a small dimension.

FIG. 4a is a top view of the detector row 36. The detector row 36 comprises a line of light sensitive pixels 37.

On the front face of a fibre optic 74, a phosphorus layer 76, which converts X-ray light into visible light, is applied. The fibre optic 74 is in the shape of a very slender right-angled triangle, with an acute angle at one end of the hypotenuse of about 2°. The individual fibres of the fibre optic run parallel to the hypotenuse. The fibre optic ends at the rear of the phosphorus layer 76 are thus ellipses, the major axes of which are significantly greater than their minor axes.

The lower end of the fibre optic 74 in FIG. 4 is cut off perpendicularly to the fibre direction. The corresponding transverse face of the fibre optic 74 carries the detector row 36, which can be in the form of a CCD component.

As a modification of the embodiments described above, it could also be considered that even in the case of digital image acquisition, the movement of the film holder 26 is retained. In the case of such a cartridge unit, to ensure that the detector row nevertheless remains behind the recording slit 32 when the X-ray source and cartridge unit are rotated, the detector row can be movably attached to the film holder, and moved on the film holder via a threaded spindle of the same gradient as the threaded spindle 28, with opposite speed to the movement of the film holder 26. The total speed of the detector row 36 is thus zero.

The detector row can also be joined rigidly to the housing 24 of the cartridge unit 20, using pins or other mechanical means, so that it remains behind the recording slit 32.

It would also be conceivable to press the detector row onto the rear of the recording slit 32 by means of a foamed material which is transparent to X-rays, so that it does not move.

With these embodiments, it is possible to produce the main components of classic cartridge units 20 and cartridge units with which digital image processing is possible exactly alike and in relatively large numbers of units.

In the case of the embodiments described above, a rotary encoder was provided, and its output signal was used in combining the total image out of the individual slit-shaped partial images to address a memory.

If a motor 22 which runs very constantly is used to rotate the X-ray source and cartridge unit, the rotary encoder 38 can be omitted. Then, to address the memory 58, a free-running clock generator, the output signal of which corresponds to the rotary position of the X-ray source and cartridge unit, can simply be used.

In other words: if the motor 22 runs with precisely specified time dependency (in particular at very constant speed), a timer can take over the function of the position meter (directly or by addressing a time/distance table).

In the case of this variant, it is then possible to compensate for changes (which are caused by the overall kinematics of the panoramic X-ray machine) of the speed of the cartridge feed within a revolution, by using a correction table, in which these variations are stored in advance.

In the case of the embodiment according to FIG. 5, device components which are described above are again described with the same reference symbols, and do not need to be described again in detail.

A detector holder 26' has the smooth external geometry of a classic panorama cartridge (film carrier 26). It rests, locked or frictionally engaged, in a cartridge carrier 77. The latter slides with guiding grooves 78 on guiding ribs 80 of the housing 24, which like the cartridge carrier 77 is open on one side in the guiding direction, to make it possible to insert and remove the classic panorama cartridges.

The detector holder 26' itself has on its front guiding grooves 82, which receive sliding guiding shoes 84 of a detector cradle 86. Like the film holder 26 as a whole, this is made of a material which is transparent to X-rays, and is of small dimension (e.g. 8 to 10 mm) in the guiding direction compared with the detector holder 26'.

The front side of the detector cradle 86 carries, at top and bottom, a connecting pin 88 which is pretensioned by a spring, and which can engage with the recording slit 32 to lock the detector cradle 86 there.

In the upper end section, the detector cradle 86 is provided with a light barrier 90 which works in reflection with a ruled grating 92, which is provided on the front of the detector holder 26' and runs in the guiding direction.

These parts, together with an up/down counter 94, form a position encoder 38, which measures the position of the detector holder 26', which is finally moved by the threaded spindle 28 and a cartridge carrier drive unit 96 which works with it.

In the lower end section, the detector cradle 86 has a forward-facing trigger diode 98, which starts a recording when it is struck by X-ray light.

Its output signal, like the output signals of the position encoder 38 and detector row 36, are output to the symbol concatenation circuit 40 and transmitted from there to an evaluation unit, as described above with reference to FIG. 2.

It can be seen that the recording unit according to FIG. 5 can work with both classic X-ray films and digital image acquisition. In the first case, a panorama cartridge (film carrier 26) equipped with an X-ray film is pushed into the cartridge carrier 77; in the second case, a recording unit with a pseudo-film carrier, the detector carrier 26', which has the same external geometry as the panorama cartridge and carries the freely movable detector cradle 86.

The latter locks with the recording slit 32 via the connecting pins 88. When the detector carrier 26' is moved in the course of generating a panoramic image, the position encoder 38 outputs a signal which is used to store the pixel signals of the detector row 36 in the memory 58, and thus to combine the panoramic image out of the individual image columns.

As may be seen from FIG. 5A, the ruled grating 92 is provided with a number of straight marks 93 cooperating with the light barrier 90.

If conversion of the image into the conventional quadratic pixel format is desired, the corresponding image signals can be determined by interpolation.

In the case of the embodiments described above, one detector row was assumed. Instead, of course, detector arrays including multiple detector rows can be used. Then with these, the information which is associated with the individual rows is shifted in the longitudinal direction of the array at the speed with which the film holder 26 would move. This can again be done on the basis of a table, in which the speeds of various X-ray machines are held.

The shifted signals can then be added in the correct columns, to obtain an image column with improved signal/noise ratio.

To synchronise the corresponding control program of the detector array with the X-ray exposure, for instance the corresponding program can be started when X-ray intensity values greater than zero are identified by the detector array, or when the trigger diode 98 or another start sensor responds.

In another modification, in the cartridge unit 20 a position sensor, which measures the relative position of the sensor to the cartridge and transmits it digitally, can be provided, similarly to what is described with reference to FIG. 1 for the simple case that the axis of the shaft 18 is fixed in space. In these conditions, the position sensor automatically generates the correction table for the cartridge feed and the clock signals of the detector array.

As shown above, in the case of the panoramic X-ray machine described above there is no galvanic connection between the components which are used for digital image acquisition and the actual X-ray machine.

To operate the components which are used for image acquisition independently of the mains, known battery types which are adequate from the point of view of storage capacity and geometrical dimensions can be used.

If rechargeable batteries are used, contacts can be provided on the housing 24 of the cartridge, so that the battery can be charged in a charging station after the cartridge is removed.

Alternatively, a low voltage socket, to which a charger can be connected as required, can be provided on the cartridge. Obviously, during charging, which preferably takes place at night, the X-ray device must not be operated.

On the cartridge, a display which signals low voltage of the power supply can be provided. To reduce the power consumption, the cartridge unit 20 is designed so that it has three operating states: "OFF", "STANDBY", "ACTIVE".

For instance, the machine can be switched from the standby state to the active operating state if an additionally integrated X-ray sensor signals the presence of an X-ray signal, or if a key on the cartridge housing is operated. In the active operating state, the image signal is actually converted and transmitted to the processing unit.

Switching back into the standby state can take place either under time control (e.g. after 30 s) or because the X-ray signal of the X-ray sensor or the detector row drops out when the program of the panorama machine is ended.

For a long operating duration of the cartridge unit 20 until the next charging, it is also useful to use semiconductor sensors with low power consumption, e.g. components in CMOS technology.

Above, data transmission from the detector row and rotary encoder to the processing unit through a radio network was discussed. If the device-side modem parts, 44 and if appropriate 66, are chosen so that they are wireless LAN modem parts, the counterpart modem parts can be formed by corresponding interfaces, which are already included as standard in many PCs and notebooks. Thus no additional costs are incurred on the processing side.

Instead of radio data transmission, infrared data transmission can be used. The device-side modem part and the evaluation-side modem part are then corresponding commercially available IR modem parts. With a view to good data transmission conditions, an IR modem part which is connected via a cable can be used on the evaluation side.

Above, the invention was described with reference to production of panoramic recordings in the dental field. Obviously, the recording device according to the invention can not only be used for panoramic recordings, but equally for other applications in medicine or materials testing where an extended image is generated from a sequence of slit-shaped partial images, e.g. an ECPH X-ray device.

It is to be understood that additional embodiments of the high-speed door assembly described herein may be contemplated by one of ordinary skill in the art and that the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

The invention claimed is:

1. A panoramic recording device for a panoramic X-ray machine—comprising:
   a cartridge unit which has a recording slit, an X-ray detection device which is arranged behind the recording slit, and a position acquisition means to capture the position of the cartridge unit,
   wherein the detection device includes at least one detector row which is shaped according to the shape of the recording slit,
   wherein the position acquisition means provides an electrical output signal which corresponds to a rotary position, and
   wherein output signals of the detector row and the position acquisition means are transmitted wirelessly to a processing unit wherein the detector row is in the form of a narrow array, and
   wherein the detector row includes a readout circuit and said readout circuit shifts pixel information of the array associated with each individual detector row, which runs parallel to the recording slit, according to the output signal of the position acquisition means and wherein the shifted pixels are added in correct columns, to obtain an image column with improved signal/noise ratio.

2. The recording device of claim 1, wherein the processing unit includes a memory having memory cells which store image signals which the detector row provides, being addressed by a signal which is derived from the output signal of the position acquisition means.

3. The recording device of claim 2, wherein the position acquisition means is provided on the cartridge unit, and the output signals of the detector row and position acquisition means are combined via a concatenation circuit into a data packet, which is transmitted via a single data transmission channel of the processing unit.

4. The recording device of claim 2, wherein the position acquisition means is spatially separated from the cartridge unit, and the output signals of the detector row and position acquisition means are fed via separate transmission channels to the processing unit.

5. The recording device of claim 2, wherein the detector row is connected to a fibre optic having an axis which is inclined at a small angle to an axis of the recording slit, and which has an end surface which is essentially perpendicular to the axis of the fibre optic, on which end surface the detector row is arranged essentially transversely to a longitudinal axis of the slit.

6. The recording device of claim 1, wherein the position acquisition means is provided on the cartridge unit, and the output signals of the detector row and the position acquisition means are combined via a concatenation circuit into a data packet, which is transmitted via a single data transmission channel of the processing unit.

7. The recording device of claim 6, wherein the cartridge unit movably carries a first cradle, on which there is second cradle which carries the detector row, and which is movable parallel to the first cradle, and which is capable of being blocked by the recording slit, is arranged.

8. The recording device of claim 7, wherein the position acquisition means includes a ruled grating which is supported by the cartridge unit, and a line reading head which is connected to the second cradle.

9. The recording device of claim 7, wherein the detector row is connected to a fibre optic having an axis which is inclined at a small angle to an axis of the recording slit, and which has an end surface which is essentially perpendicular to the axis of the fibre optic, on which end surface the detector row is arranged essentially transversely to a longitudinal axis of the slit.

10. The recording device of claim 6, wherein the detector row is connected to a fibre optic having an axis which is inclined at a small angle to an axis of the recording slit, and which has an end surface which is essentially perpendicular to the axis of the fibre optic, on which end surface the detector row is arranged essentially transversely to a longitudinal axis of the slit.

11. The recording device of claim 1, wherein the position acquisition means is spatially separated from the cartridge unit, and the output signals of the detector row and the position acquisition means are fed via separate transmission channels to the processing unit.

12. The recording device of claim 11, wherein the cartridge unit has a film holder capable of being connected to or disconnected from a shaft which carries the cartridge unit, according to choice.

13. The recording device of claim 11, wherein the detector row is connected to a fibre optic having an axis which is inclined at a small angle to an axis of the recording slit, and which has an end surface which is essentially perpendicular to the axis of the fibre optic, on which end surface the detector row is arranged essentially transversely to a longitudinal axis of the slit.

14. The recording device of claim 1, wherein the detector row is connected to a fibre optic having an axis which is inclined at a small angle to an axis of the recording slit, and which has an end surface which is essentially perpendicular to the axis of the fibre optic, on which end surface the detector row is arranged essentially transversely to a longitudinal axis of the slit.

* * * * *